(12) United States Patent
Midgette et al.

(10) Patent No.: US 9,533,136 B2
(45) Date of Patent: Jan. 3, 2017

(54) SINTERED POROUS POLYMERIC CAPS AND VENTS FOR COMPONENTS OF MEDICAL DEVICES

(71) Applicant: Porex Corporation, Fairburn, GA (US)

(72) Inventors: William G. Midgette, Grayson, GA (US); GuoQiang Mao, Peachtree City, GA (US); Avi Robbins, Atlanta, GA (US); Jack Chan, Peachtree City, GA (US)

(73) Assignee: Porex Corporation, Fairburn, GA (US)

( * ) Notice: Subject to any disclaimer, the term of this patent is extended or adjusted under 35 U.S.C. 154(b) by 60 days.

(21) Appl. No.: 14/141,872

(22) Filed: Dec. 27, 2013

(65) Prior Publication Data

US 2014/0188089 A1  Jul. 3, 2014

Related U.S. Application Data

(60) Provisional application No. 61/746,677, filed on Dec. 28, 2012, provisional application No. 61/746,695, (Continued)

(51) Int. Cl.
*A61M 39/16* (2006.01)
*A61M 39/20* (2006.01)
(Continued)

(52) U.S. Cl.
CPC ............ *A61M 39/16* (2013.01); *A61L 2/18* (2013.01); *A61L 2/20* (2013.01); *A61L 31/048* (2013.01);
(Continued)

(58) Field of Classification Search
CPC ..... A61M 39/16; A61M 39/20; A61L 31/048; A61L 2/18; A61L 2/20; A61L 31/146; A61L 5/3146; A61L 5/3202; A61L 5/321; A61L 2/00; A61L 2/0005
(Continued)

(56) References Cited

U.S. PATENT DOCUMENTS

| 3,631,654 A | 1/1972 | Riely et al. |
|---|---|---|
| 4,443,515 A | 4/1984 | Atlas |

(Continued)

FOREIGN PATENT DOCUMENTS

| EP | 111723 | 6/1984 |
|---|---|---|
| EP | 1568392 | 8/2005 |

(Continued)

OTHER PUBLICATIONS

Standard Test Method for Evaluating the Bacterial Filtration Efficiency (BFE) of Medical Face Mask Materials, Using a Biological Aerosol of *Staphylococcus aureus*. ASTM International Designation: F2101-14. 2014.*

(Continued)

*Primary Examiner* — Jill Warden
*Assistant Examiner* — Jacqueline Brazin
(74) *Attorney, Agent, or Firm* — Kilpatrick Townsend & Stockton LLP

(57) ABSTRACT

The present application provides a device and methods of making and using these devices. The devices comprise porous caps and porous vents made from sintered porous polymeric media comprising plastic particles, elastomeric particles or a combination thereof. These devices are used with medical devices or components thereof to provide ease of use, resistance to infection, sterilization and venting.

17 Claims, 7 Drawing Sheets

Related U.S. Application Data filed on Dec. 28, 2012, provisional application No. 61/835,883, filed on Jun. 17, 2013.

(51) Int. Cl.

| | | |
|---|---|---|
| *A61L 2/20* | (2006.01) | |
| *A61L 31/14* | (2006.01) | |
| *A61L 31/04* | (2006.01) | |
| *A61L 2/18* | (2006.01) | |
| *A61M 5/31* | (2006.01) | |
| *A61M 5/32* | (2006.01) | |
| *A61M 5/14* | (2006.01) | |
| *A61M 39/00* | (2006.01) | |

(52) U.S. Cl.
CPC ........... *A61L 31/146* (2013.01); *A61M 5/3146* (2013.01); *A61M 5/321* (2013.01); *A61M 5/3202* (2013.01); *A61M 39/20* (2013.01); *A61M 2005/1403* (2013.01); *A61M 2005/3123* (2013.01); *A61M 2039/0036* (2013.01); *A61M 2039/205* (2013.01)

(58) Field of Classification Search
USPC .................................. 422/28, 1, 26; 604/39
See application file for complete search history.

(56) References Cited

U.S. PATENT DOCUMENTS

| | | | |
|---|---|---|---|
| 4,682,980 A | | 7/1987 | Suzuki |
| 4,724,114 A | | 2/1988 | McFarland et al. |
| 4,820,577 A | * | 4/1989 | Morman et al. ............... 442/400 |
| 5,065,783 A | | 11/1991 | Ogle, II |
| 5,175,046 A | | 12/1992 | Nguyen |
| 5,552,115 A | * | 9/1996 | Malchesky ............ A01N 37/16 422/1 |
| 5,750,585 A | | 5/1998 | Park et al. |
| 5,797,347 A | | 8/1998 | Ochi |
| 5,824,328 A | | 10/1998 | Levy |
| 5,836,929 A | | 11/1998 | Bewick-Sonntag et al. |
| 5,939,086 A | | 8/1999 | Levy |
| 5,998,032 A | | 12/1999 | Hansen et al. |
| 7,114,701 B2 | | 10/2006 | Peppel |
| 7,780,794 B2 | | 8/2010 | Rogers et al. |
| 7,981,090 B2 | | 7/2011 | Plishka et al. |
| 8,828,327 B2 | * | 9/2014 | Colantonio ............... A46B 9/02 422/294 |
| 2002/0134175 A1 | * | 9/2002 | Mehra ................... B01L 3/0275 73/863.85 |
| 2004/0173556 A1 | | 9/2004 | Smolko et al. |
| 2006/0184116 A1 | * | 8/2006 | Takagi .............. A61M 25/0618 604/110 |
| 2007/0112333 A1 | | 5/2007 | Hoang et al. |
| 2007/0202177 A1 | | 8/2007 | Hoang |
| 2008/0027399 A1 | * | 1/2008 | Harding .............. A61M 39/045 604/265 |
| 2008/0038167 A1 | | 2/2008 | Lynn |
| 2008/0085680 A1 | | 4/2008 | Kim et al. |
| 2008/0132880 A1 | | 6/2008 | Buchman |
| 2008/0199363 A1 | * | 8/2008 | Mao ......................... B01J 20/26 422/400 |
| 2009/0008393 A1 | * | 1/2009 | Howlett ................ A61M 39/20 220/380 |
| 2010/0036330 A1 | | 2/2010 | Plishka et al. |
| 2010/0297577 A1 | | 11/2010 | Cohen |
| 2012/0130305 A1 | | 5/2012 | Bonnal et al. |

FOREIGN PATENT DOCUMENTS

| | | | |
|---|---|---|---|
| GB | 1401382 | | 7/1975 |
| WO | WO 2011/150184 | * | 12/2011 |
| WO | 2013067106 | | 5/2013 |

OTHER PUBLICATIONS

Air resistance of paper (Gurley method) (Revision of T 460 om-02). TAPPI. 2006.*
International Patent Application No. PCT/US2013/077984, International Search Report and Written Opinion mailed on Apr. 22, 2014, 11 pages.
PCT International Patent Application No. PCT/US2013/077984, International Preliminary Report on Patentability, mailed on Jul. 9, 2015, 8 pages.

* cited by examiner

SINTERED POROUS POLYMERIC CAPS AND VENTS FOR COMPONENTS OF MEDICAL DEVICES

PRIOR RELATED APPLICATIONS

The present application claims the benefit of priority of U.S. Provisional Patent Application Ser. No. 61/746,677, filed Dec. 28, 2012, U.S. Provisional Patent Application Ser. No. 61/746,695, filed Dec. 28, 2012, and U.S. Provisional Patent Application Ser. No. 61/835,883, filed Jun. 17, 2013, each of which is incorporated by reference herein in its entirety.

FIELD OF THE INVENTION

The present application provides devices and methods of making and using these devices. The devices comprise porous caps and porous vents made from sintered porous polymeric media comprising plastic particles, elastomeric particles or a combination thereof. These devices are used with medical devices or components thereof to provide ease of use, resistance to infection, sterilization and venting.

BACKGROUND OF THE INVENTION

Many medical devices have components such as needleless access ports and connection ports in different locations for liquid injection, liquid sampling, or liquid drainage. These needleless access ports generally have rubber valves or stoppers that prevent liquid from leaking, and also allow needleless syringes to access the port for liquid injection or liquid sample collection. These devices include but are not limited to infusion bags or systems, intravenous (IV) catheters, chest tubes, drainage tubes, connection ports including luer locks, ear tubes, urine bags, or urine collection systems. The embodiments of the invention described below are intended for use with these and any other appropriate devices. Contamination at these liquid access ports and luer locks is a major cause of healthcare-associated infection (HAI). HAI causes a number of deaths and creates a huge cost for healthcare. One of the major reasons for infection is incomplete or unacceptable disinfection during the liquid injection process. Many have attempted to reduce the chances of HAI by making the antiseptic procedure easy and simple to reduce the potential for human error. For example, U.S. Publication No. 2007/0112333 describes a patient fluid line access valve antimicrobial cap and cleaner. This cap contains a dry pad impregnated with antimicrobial agent. This solid non-porous cap covers the access portion when the port is not in use. Other examples of needleless access ports are shown and described in U.S. Patent Application Publication No. 2009/0008393, which describes a pair of nestable caps; U.S. Pat. No. 7,114,701, which describes needleless access port valves with a venting hole; U.S. Pat. No. 7,981,090, which describes luer activated devices with antimicrobial agents; and U.S. Pat. No. 7,780,794, which describes medical cleaning devices that include a non-porous cap and compressible cleaning materials. This cap can be used to clean the site with an embedded cleaning agent. However, improvements to needless access port caps are still needed in order to reduce infections and for ease of use.

Many medical devices that handle liquid need to be vented in order to allow stable and good liquid flow. Two common devices that handle liquid are infusion bags and urine bags. Infusion bags are used to hold liquids to be delivered into the body, such as an intravenous (IV) bag, a chemotherapy bag, or any other liquid substance to be delivered to a patient. The bag needs to be vented in order to help balance the pressure. Urine bags need vents in order to allow urine flow into the reservoir. Tubing and luer locks also need vents. Tubing and luer locks are common locations for trapping air bubbles. Air bubbles trapped in the IV kits are potentially dangerous because air bubbles delivered into the vascular system can pose serious health risks.

Many of these medical devices have venting systems, but they are not always optimal. For example, some urine bags have a vent in the bag, and infusion bags have a vent on one end of the bag. The vents help balance the pressure inside and outside the bag and reduce liquid flow resistance. However, many of these vents in the bags are not satisfactory. In some instances, they are located too far away from where they are needed in order to affect liquid flow in narrow tubing. They also do not help in removing the trapped air bubbles in the tubing or luers. Some of the currently available infusion bags or containers need vents, and in many developing countries, the nurses have to punch a needle into the infusion bag to provide venting. However, this practice increases the chance of contamination from the air. Additionally, even for bags that do not require a vent, a vent would provide better liquid flow.

There have been a number of attempts to improve needleless access ports and needleless connectors. U.S. Patent Application Publication 2010/0036330 describes a needleless connector intended to prevent retro flow using a vent in a housing. U.S. Pat. No. 5,065,783 describes a valve with a self-sealing cannula using a rubber material. U.S. Patent Application Publication No. 2012/0130305 describes an apparatus with a membrane vent. However, all these materials used for vents and methods of venting disclosed in the prior art are different from those described herein. There also have been a number of methods for disinfecting medical devices. U.S. Patent Application Publication No. 2009/008393 describes an antiseptic cap design for a catheter. U.S. Patent Application Publication No. 2008/0132880 discloses catheter cleaning devices. U.S. Publication 2008/0085680 describes a needless hub disinfection device/cap. U.S. Patent Application Publication No. 2008/0038167 discloses a disinfection cap. U.S. Patent Application Publication No. 2008/0027399 describes a valve cleaning device. U.S. Patent Application Publication No. 2007/0202177 describes antimicrobial compositions and methods for locking catheters. All of these methods are not satisfactory.

Improvements to medical device access ports, including methods for maintaining cleanliness, for disinfecting and for venting are needed.

SUMMARY

The present invention solves these problems and provides devices, systems and methods for using porous polymeric media as a porous cap or porous vent in medical devices or components thereof.

In one embodiment, the porous cap is used with components such as liquid access and connection ports in a medical device. The porous cap allows sterilization chemicals to sterilize the port it covers, prevents bacterial growth, and keeps contaminants away from liquid access and connection ports. In one embodiment, the porous cap is made of sintered porous plastic. In another embodiment the porous cap is made of sintered elastomeric materials. In another embodiment the porous cap is made is sintered porous plastic in combination with an elastic material. The porous cap may have antimicrobial additives that provide antimicrobial activity and protect the liquid access ports from bacterial contamination. In some instances, the cap can relieve a nurse or other medical personnel from the routine cleaning process that is required for disinfection. The porous cap also keeps the liquid access port dry and prevents moisture build up and bacteria and pathogen accumulation. The cap is designed to be easily removed and applied to the access port. The porous cap allows gas, such as moisture and ethylene oxide (EO) sterilization gas to pass through the cap, contact and sterilize a surface of the medical device. Since the porous cap is permeable, it also permits a gas to escape, thereby preventing gas residue such as EO residue which could deleteriously affect certain plastics.

Any liquid access port, luer, line, catheter or tube may be covered with the porous cap of the present invention. These include, without limitation, an intravascular line, a cerebroventricular line, a gastrointestinal line, a peripherally inserted central catheter (PICC line), a urinary catheter, connection ports including luer locks, ear tubes, a drainage tube, a shunt, a percutaneous endoscopic gastrostomy (PEG) tube or an extension thereof such as a jejunal extension tube (PEG-J), a nasogastric tube, endotracheal tube, laparoscope or another tube. Any tube or port capable of use in a patient may be protected with these porous caps.

Tubing, catheters, luer locks and liquid access ports have open ends and are common places for infection in a medical device. Once a medical device package is opened, these tubing, catheters, luer locks and liquid access ports are exposed to the air without protection. In one embodiment, the present invention provides porous caps and methods of using them which reduces potential infections from these components of medical devices. Medical devices or components thereof, such as tubing, catheters, lines, luer locks and liquid access ports are covered with the porous caps of the present invention before they are packaged in a medical packaging and sterilized with common sterilization methods, such as ethylene oxide (EO) gas, gamma and e-beam sterilization. Since the porous caps are highly permeable they do not interfere with sterilization procedures. Once a medical device package is opened, the porous caps continue to protect medical devices or components thereof from contamination. The cap can be removed from these devices when the device is needed in the medical procedure. These porous caps reduce the chance of infection at these locations because some of those locations in a medical device may be used hours or even days in a non-sterilized environment after the package is opened, such as, intravenous therapy devices. In surgical kits, several medical devices may be packaged and sterilized using conventional techniques. Many medical procedures have delays in opening medical packaging and using devices or some components of the medical devices. These delays increase the chance for infection because the medical devices may be exposed to a non-sterilized environment for a period of time. Use of the porous caps of the present invention to protect medical devices within packaging reduces the contamination risk during this period of time.

The porous vents of the present invention can be used in medical devices which require or benefit from the use of a vent. Such medical devices include, but are not limited to, needleless access ports, urine bags, and infusion bags. The porous vents may be flexible or rigid, depending on the requirements of the application.

The porous vents can make liquid flow quicker and more smoothly through narrow tubing and can reduce or eliminate the labor of medical personnel to control liquid flow in medical devices and to disinfect medical devices. In one embodiment, porous vents are used in needleless access ports. In various embodiments, these porous vents may be in the form of a cap, a plug, or a syringe filter. These porous vents can provide a bacterial barrier and/or a liquid barrier. These porous vents can wick antiseptic agents and deliver them to both internal and external surfaces of needleless access ports.

In one embodiment, the porous vent is made of sintered porous plastic. In another embodiment the porous vent is made of elastomeric materials. In another embodiment the porous vent is made is sintered porous plastic in combination with an elastic material. The porous vent may have antimicrobial additives that provide antimicrobial activity and protect the liquid access ports from bacterial contamination.

Other objects and advantages of the invention will be apparent from the following summary and detailed description of the embodiments of the invention taken with the accompanying drawing figures.

DETAILED DESCRIPTION

Figure 1:
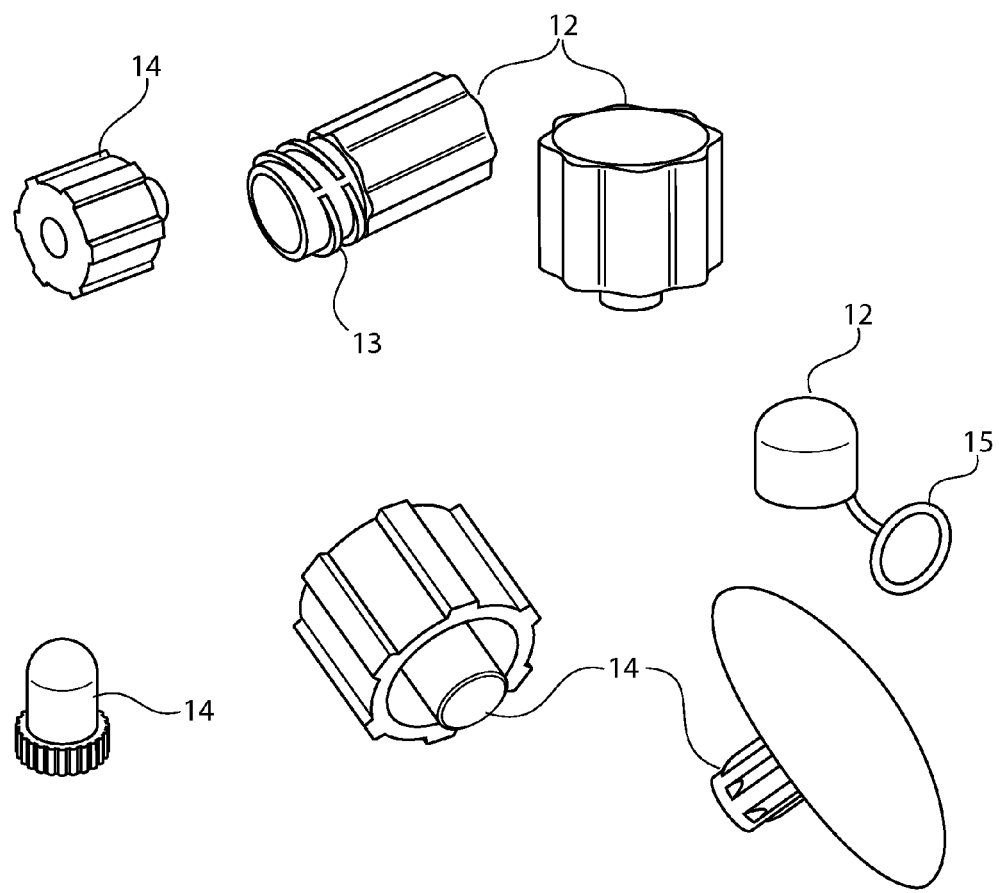
FIG. 1. Schematic representations of shapes for sintered porous polymer caps 12 or insertion vents 14 for a needleless access port or connector plugs, some with threads 13 or attachment means 15 to attach to a medical device.
Figure 2:
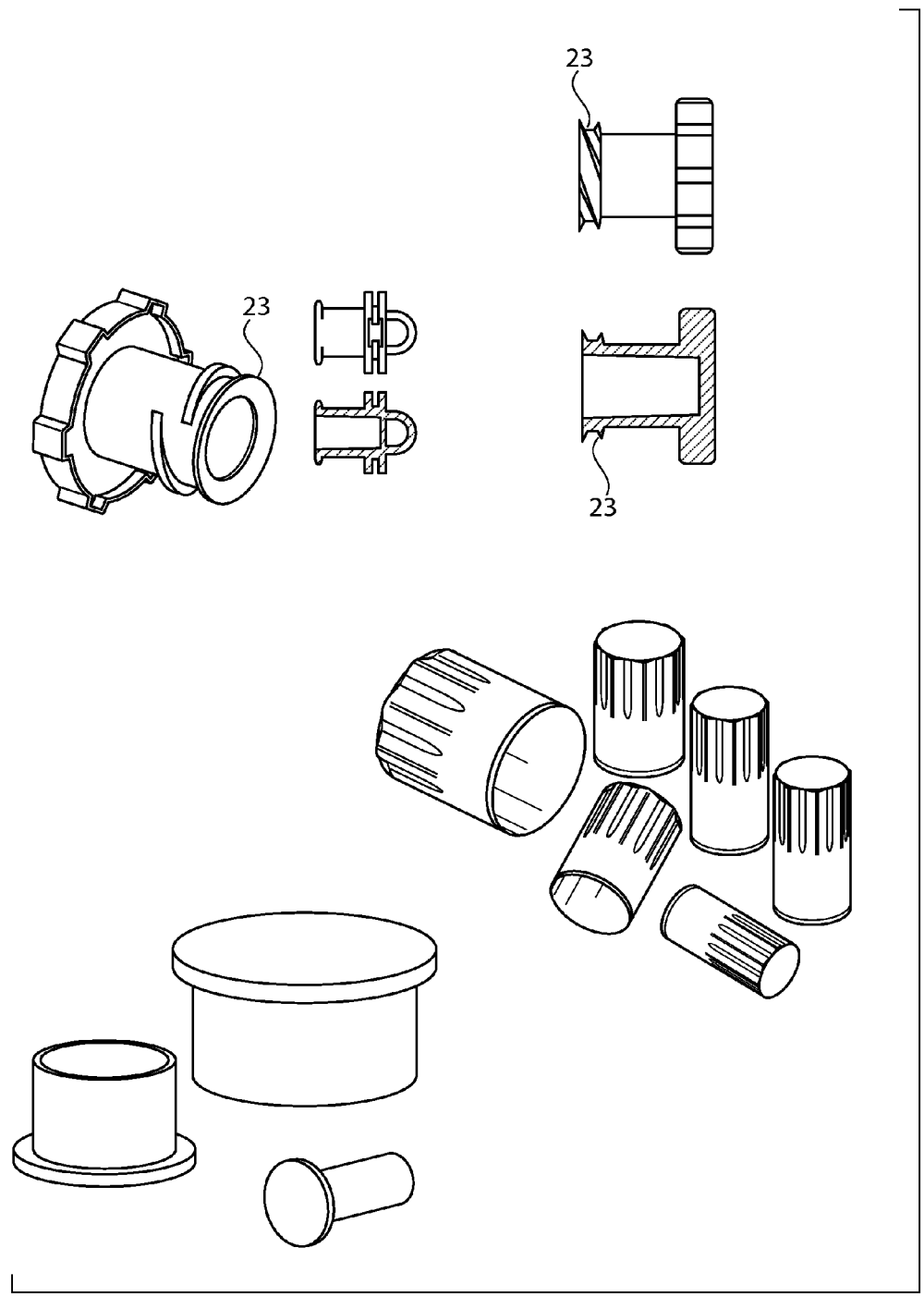
FIG. 2. Schematic representations of shapes for sintered porous elastomeric caps, some with threads 23.
Figure 3:
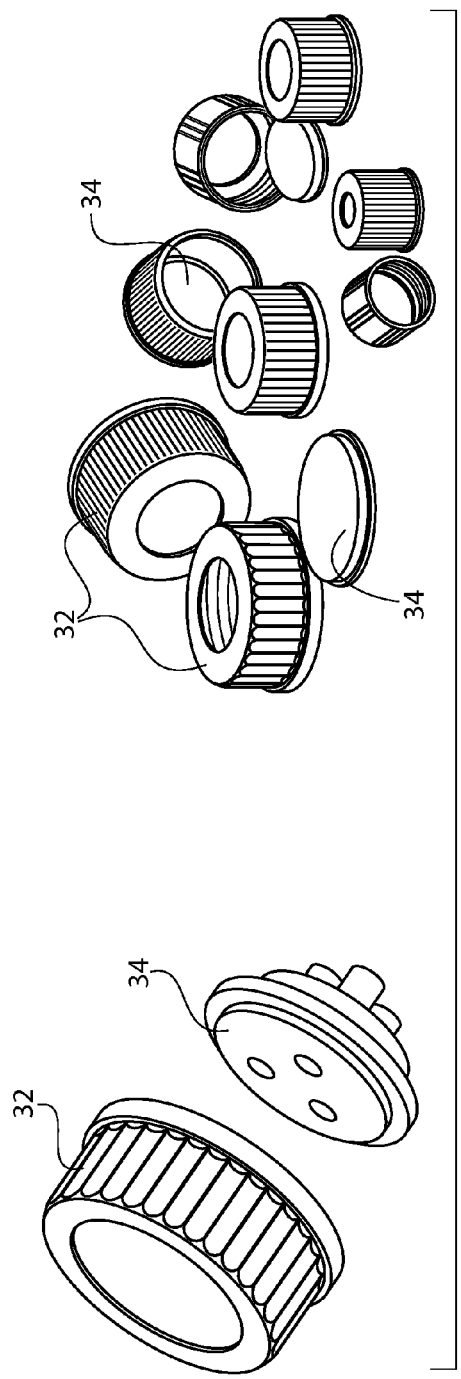
FIG. 3. Examples of a liquid access port cap 32 with an injection molded non-porous plastic or elastomeric housing and sintered porous vents 34 as filters, discs, or liners.
Figure 4:
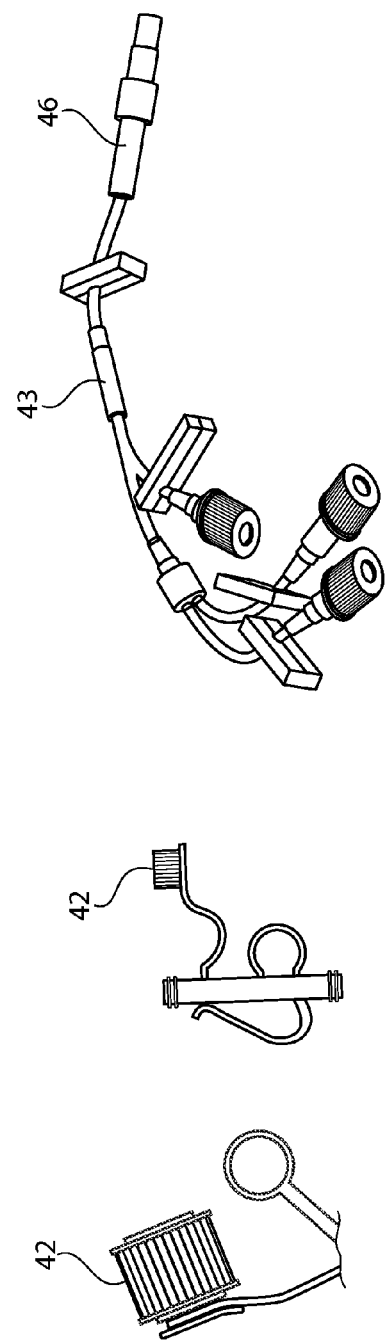
FIG. 4. Examples of a liquid access port cap 42 and liquid access port 43 connected by coupling devices 46 or by a cap 42 comprising a porous element FIG. 5. Schematic representation of antimicrobial efficacy against *Pseudomonas* sp for sintered porous media (UHM-WPE) with silver based antimicrobial agent (Agion) based on the ASTM 2149 test method. After 4 and 20 hours, all *Pseudomonas* sp were killed.
Figure 5:
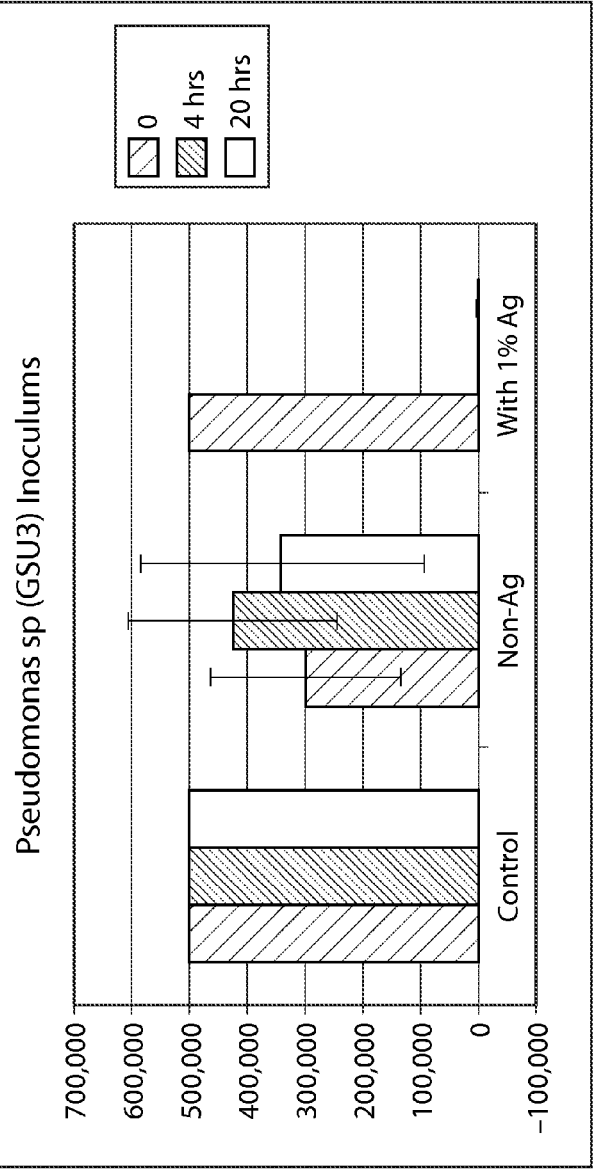
Figure 6:
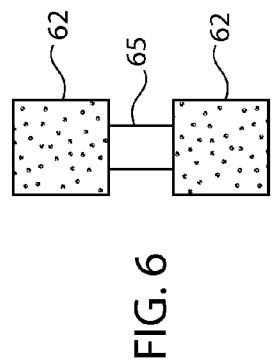
FIG. 6. Sample representation of sintered porous elastomeric cap 62 made from 100% ethylene vinyl acetate (EVA) for covering openings of medical devices such as a tube 65.
Figure 7:
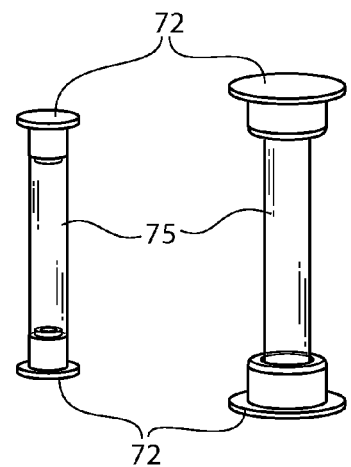
FIG. 7. Schematic representation of a shape for a sintered porous polymeric cap 72 for covering openings of medical devices, such as a tube 75. The cap has a design which is easy to remove using fingers.
Figure 8:
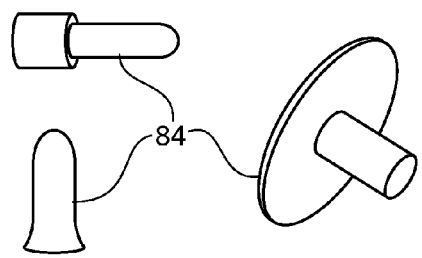
FIG. 8. Schematic representation of shapes for a sintered porous polymer vent 84.
Figure 9:
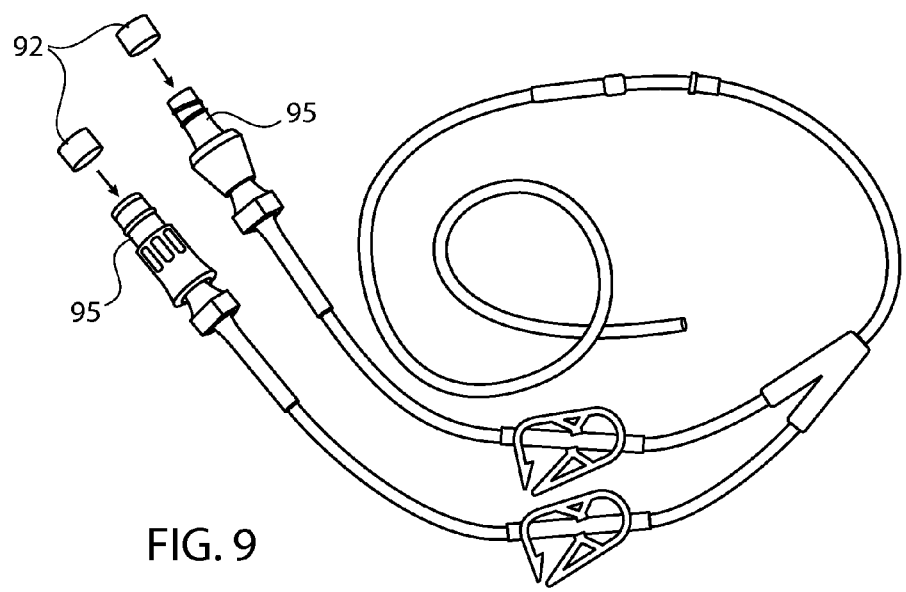
FIG. 9. Schematic representation of porous caps 92 covering catheters 95.
Figure 10:
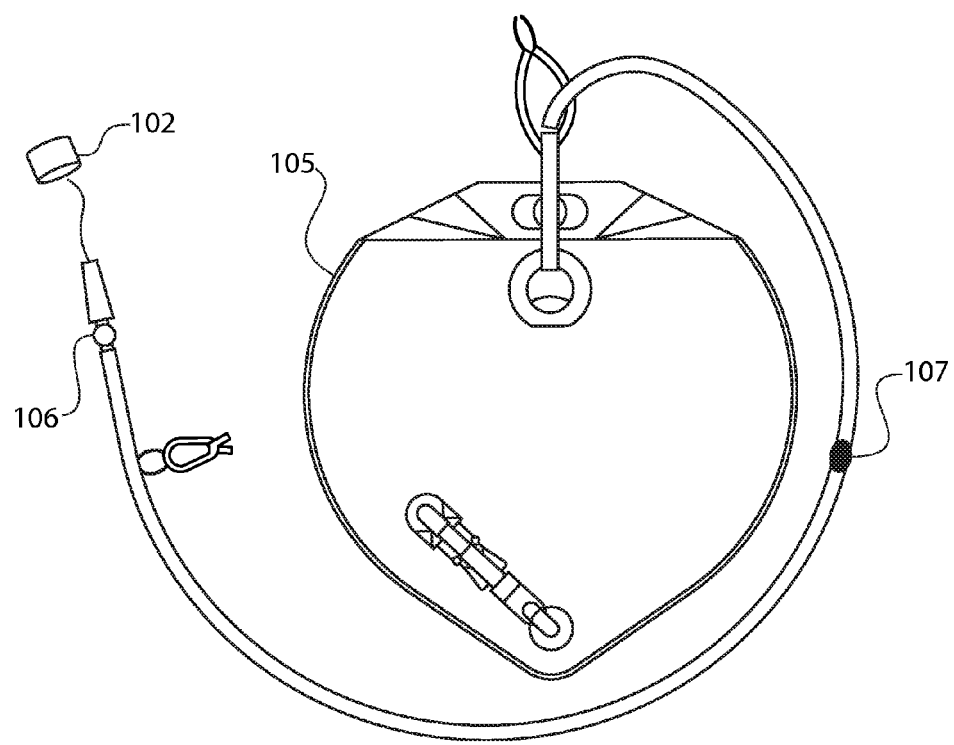
FIG. 10. Locations for porous caps 102 and vents associated with a urine collection bag 105. The porous 102 cap can be located over the end of the tube. Porous vents can be located at needleless access ports 106, 107.
Figure 11:
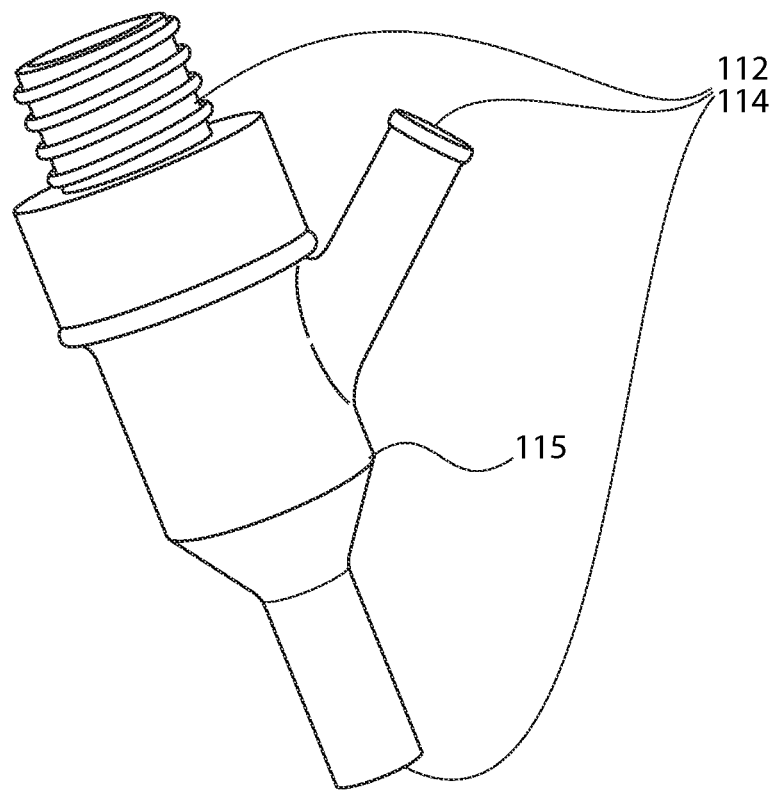
FIG. 11. Porous caps 112 and porous vents 114 can be used at multiple locations in a needleless access port 115. Porous caps may function as porous vents.

The present invention provides devices, systems and methods for using porous polymeric media as a porous cap or porous vent in medical devices or components thereof. Medical devices or components thereof include those devices and components that would benefit from use of the porous caps or porous vents of the present invention. Such medical devices include, but are not limited to, needleless access ports, urine bags, and infusion bags, tubing, catheters, luer locks and liquid access ports. Any liquid access port, luer, line, catheter or tube many be covered with the porous cap or receive the porous vent of the present invention. These include, without limitation, an intravascular line, a cerebroventricular line, a gastrointestinal line, a peripherally inserted central catheter (PICC line), a urinary catheter, a drainage tube, a shunt, a PEG tube, a nasogastric tube, endotracheal tube, laparoscope or another tube. Any tube or port capable of use in a patient may be protected with these porous caps or porous vents.

Porous Cap Materials

Embodiments of the invention relate to using sintered porous materials as a cap for medical fluid access sites, particularly to access sites having needleless access ports. In contrast to some of the other needleless port caps on the market, such as the Curos® Port Protector (Ivera Medical Corporation, San Diego, Calif.), the present invention uses a dry porous media with optional antimicrobial additives as a cap for the access port. The porous media in the cap is gas permeable and allows sterilization gas to sterilize the area it covers. The porous cap prevents bacteria from directly depositing on the area it covers. In yet another embodiment, the porous cap comprising porous media which permits passage of sterilization gas kills the bacteria that may already be present on the surface. In another embodiment, the porous cap with antimicrobial additives kills the bacteria that may already be present on the surface.

In one embodiment, the porous cap is made of sintered porous plastic. In another embodiment the porous cap is made of an elastomeric material. In yet another embodiment the porous cap is made of sintered porous plastic in combination with an elastomeric material. Inclusion of elastomeric materials generally increases compressibility of the cap. This is in contrast to the non-porous caps of the prior art, which used solid non-porous media or foam. The porous cap does not interfere with chemical sterilization processes because the porous cap has high gas permeability.

The cap may either be completely formed from a sintered porous material, or it may have only selected portions that are formed from sintered porous material. If sintered porous material is used to form the entirety of the cap, the entire cap may provide breathability and venting functions.

Sintered porous plastic materials generally are rigid and self-supporting. They can provide a good barrier between the environment and liquid access ports. In some applications, a flexible and stretchable porous material is preferred for its flexibility and elasticity. In this case, sintered porous elastomeric material is used. Sintered porous elastomeric materials may comprise one or more elastomeric materials. Elastomeric materials that can be sintered into sintered porous elastomeric media are provided herein. In one embodiment, the sintered porous material is made of mixtures of plastic and other materials to provide porous caps with a variety of hardness, flexibility and durability. For example, the sintered porous material may be made from mixtures of plastic materials and elastomeric materials in order to produce a sintered porous material with the desired rigidity/flexibility combination and to ensure that the feel on the hand is appropriate during removal of the cap. Potential ratios of plastic materials and elastomeric materials in the sintered porous materials can vary from 9.9 to 0.1, from 9.5:0.5 to 0.5:9.5, from 9:1 to 1:9; or from 8:2 to 2:8. The elastomeric materials may be sintered elastomeric materials.

However, because some or all of these sintered porous materials can be expensive to manufacture, desirable alternate embodiments are also provided. In another embodiment, only certain portions of the cap may be formed from the sintered porous material while other parts of the cap are formed from other (potentially less expensive and/or stronger) materials. If only a portion of the cap is made from sintered porous material, the other portions of the cap may be injection molded, formed from a non-porous material, an elastomer, or formed from any other appropriate material, including but not limited to thermal setting resins, thermal plastics, and thermal plastic elastomers (TPEs).

Porous Cap Embodiments

In one embodiment, the cap is a generally rigid structure, with one open end, one closed end and a hollow cylindrical structure. The open end and hollow cylindrical structure allow the cap to be capped onto a liquid access port by friction coupling.

In another embodiment, the cap is a generally rigid structure, with one open end, one closed end and a hollow cylindrical structure. The hollow cylindrical structure has threads, which allow the cap to be capped onto liquid access port by cooperation between the cap threads and external threads on the access port.

In one embodiment, the cap is a generally rigid structure and with a male portion having threads, which allow the cap to be capped onto a liquid access port by cooperation between the male portion threads and an internal thread on the access port. In other words, the sintered porous plastic cap member can be screwed onto the needleless access port.

In another embodiment, the cap is a generally rigid structure and with a female portion having internal threads, which allow the cap to be capped onto a liquid access port by cooperation between the female portion threads and an external thread on the access port. In other words, the sintered porous plastic cap member can be screwed onto the needleless access port.

In still another embodiment, the cap is flexible and can be capped onto the liquid access port by stretching the cap. The flexibility may be imparted via one or more elastomers in the sintered porous material.

In another embodiment, the cap is capped onto or plugged into the liquid access port by a friction fit. If the cap is frictionally fit on the port, it is preferably designed to be removed easily by finger pressure.

In yet another embodiment, the cap is capped onto or plugged into the liquid access port by a snap fit and a locking mechanism.

In another embodiment, the cap is an injection molded cap with two openings and an internal thread. The injection molded portion of the cap provides the physical support for securing the cap to the port access. Porous liners or discs are provided with the cap, and one or more porous liners can be positioned to cover one of the openings at the top of the cap, such that the liner is in close contact with the liquid access port when the cap is on the port. The liner is generally made of a sintered porous plastic.

Porous Vents

The porous vents of the present invention can be used in medical devices which require or benefit from the use of a vent. Such medical devices include, but are not limited to, needleless access ports, urine bags, and infusion bags. The porous vents may be flexible or rigid, depending on the requirements of the application.

The porous vents can make liquid flow quicker and more smoothly through narrow tubing and can reduce or eliminate the labor of medical personnel to control liquid flow in medical devices and to disinfect medical devices. In one embodiment, porous vents are used in needleless access ports. In various embodiments, these porous vents may be in the form of a cap, a plug, or a syringe filter. These porous vents can provide a bacterial barrier and/or a liquid barrier. These porous vents can wick antiseptic agents and deliver them to both internal and external surfaces of the needleless access ports.

In urine bag kits, providing porous vents in needleless access ports can increase urine flow, reduce potential leakage from the urine bag because of accidental tipping by the patient, increase design flexibility, and reduce the cost.

The porous vents in this invention can comprise sintered porous plastics, sintered porous elastomeric materials, porous membranes and/or non-woven materials.

The porous vents function as vent, bacterial barrier and/or a liquid barrier. In a specific embodiment, porous media can wick antiseptic agents and deliver antiseptic agents to both internal and external surfaces of the port. In one embodiment, porous venting media provide a bacterial-free environment for the ports.

When needleless ports are not in use for sampling or injecting liquid and venting is needed, the porous media may be plugged into the ports. Porous vents inserted into the ports will keep the valve open and allow air or gas to venting out of the system, but prevent liquid from leaking out of the system. Air permeable needleless access ports provide a higher liquid flow rate in the tubing, and reduce the air bubbles that may form inside the tubing. When a sample needs to be taken or if a liquid needs to be injected into the port, the porous vent may be removed and a syringe may be applied to deliver or remove liquid from the system through the port. It has been found that using porous media as a plug or cap at needleless access ports can provide a convenient and cost effective way to vent a system through widely-used needleless access ports components in medical devices. Optionally, the porous media may be provided with an antimicrobial agent to make porous media with antimicrobial activity. Antimicrobial porous media protect liquid access ports from bacterial contamination.

Embodiments of this invention relate to improved venting methods for medical devices and components thereof by introducing a porous vent to needleless access ports. Needleless access ports or needleless connecters have a rubber mechanical valve, and the rubber mechanical valve is closed to prevent foreign particles from entering into the system, and to prevent the liquid inside the system from leaking. When samples need to be taken or additional medication needs to be added, a syringe is attached to the port, and the male portion of syringe will open the rubber mechanical valve. The rubber mechanical valve will close after the syringe is removed. There are often multiple needleless access ports in one medical device; needleless access ports can be on the liquid container or the tubing or both. Needleless access ports or connection areas usually have dead ends with dead volume. These dead end locations are likely to trap air bubbles. Trapped air bubbles will affect liquid flow and have the potential of moving into the liquid stream and into the patient's vascular system. Air bubbles in blood may cause a stroke and other unwanted consequences. Additionally, patients are generally nervous about air bubbles in the IV devices. Introducing a porous vent at a needleless access port can vent trapped air bubbles at the port and provide more stable liquid flow in the tubing and safer medical operation.

In another embodiment, porous vents may also function as port cleaning devices. The porous vents may contain one or more antimicrobial agent which can kill microbes such as bacteria and keep the port clean. The porous vent described herein may have small pores with capillary force that can wick liquid containing one or more forms of antimicrobial agents and deliver liquid forms of these antimicrobial agents to the internal and external surfaces of the port.

In yet another embodiment, porous vents may function as a port protection device. The porous vents described herein can also function as a cap and provide mechanical protection, and prevent dust and aerosol deposition on the surface of the port.

Structure and Materials of Porous Vents

The porous vent for a needleless access port can be provided in many different shapes, such as a cap, rod, hollowed rod, disk, or syringe filter. In one embodiment the porous vent can be inserted into a needleless access port to keep the needless access port open. The vent is optionally attached to the housing of the needleless access port for convenient and easy access. The vent can be also prepackaged in a sterilized package and used when needed.

Optionally, a porous vent can be permanently located in the housing of the needleless access port.

In one embodiment, the porous vent is in a cap form with a porous male portion. The male portion of the porous cap can be plugged into an access port to keep the port open to the atmosphere and provide protection for the port. The porous cap allows air by-pass, but not liquid by-pass. The porous cap may be formed of sintered porous plastic or elastomeric materials or a combination thereof.

In one embodiment, the porous vent is physically attached to the housing of the port and can easily be inserted and removed from the port. This can prevent loss of the porous vent when the port is opened for access by medical personnel. This also provides convenient access to the port.

In one embodiment, the porous vent may be flexible. A flexible porous vent is made by using elastomeric polymers or combining elastomeric polymers with plastic polymer. The vent can be in a cap form. The vent can be capped onto the liquid access port by stretching the vent.

In another embodiment, the porous vent may be rigid. A rigid porous vent is made by using plastic polymers. The rigid vent may have threads that can cooperate with threads on the liquid access port. The vent may be an injection molded cap with two openings with a porous vent provided at one of the openings. Alternatively, the vent may be frictionally fit on the port and easily removable with fingers.

Some embodiments provide a method of venting a needleless access port by inserting a porous media into the needleless valve in a needleless access port.

Other embodiments relate to a method of cleaning and disinfecting the inside and/or outside of a needleless access port by inserting a porous plastic with an antimicrobial agent into the needleless valve in the needleless access port.

Still other embodiments relate to a method of venting a fluid drainage and delivery system by venting a needless access port with sintered porous media inserted into the needleless access port.

Thermoplastic Materials that can be Used in Sintered Porous Plastic Media for Porous Caps and Porous Vents Plastics suitable for use in sintered polymeric media of the present invention, in some embodiments, comprise polyolefins, polyamides, polyesters, rigid polyurethanes, polyacrylonitriles, polycarbonates, polyvinylchloride, polymethylmethacrylate, polyvinylidene fluoride, polytetrafluoroethylene, polyethersulfones, polystyrenes, polyether imides, polyetheretherketones, or polysulfones, and combinations and copolymers thereof.

In some embodiments, a polyolefin comprises polyethylene, polypropylene, and/or copolymers thereof. Polyethylene, in one embodiment, comprises high density polyethylene (HDPE). High density polyethylene, as used herein, refers to polyethylene having a density ranging from about 0.93 g/cm$^3$ to about 0.97 g/cm$^3$. Polyethylene, in one embodiment, comprises medium density polyethylene. Medium density polyethylene (MDPE), as used herein, refers to polyethylene having a density ranging from about 0.92 g/cm$^3$ to about 0.93 g/cm$^3$. Polyethylene, in one embodiment, comprises low density polyethylene. Low density polyethylene (LDPE), as used herein, refers to polyethylene having a density ranging from about 0.91 g/cm$^3$ to about 0.92 g/cm$^3$. Polyethylene, in one embodiment, comprises linear low density polyethylene. Linear low density polyethylene (LLDPE), as used herein, refers to polyethylene having a density ranging from about 0.91 g/cm$^3$ to about 0.92 g/cm$^3$. Polyethylene, in one embodiment, comprises very low density polyethylene. Very low density polyethylene (VLDPE), as used herein, refers to polyethylene having a density ranging from about 0.89 g/cm$^3$ to about 0.91 g/cm$^3$. In another embodiment, polyethylene comprises ultrahigh molecular weight polyethylene (UHMWPE). Ultrahigh molecular weight polyethylene, as used herein, refers to polyethylene having a molecular weight greater than 1,000,000. In another embodiment, polyethylene comprises very high molecular weight polyethylene (VHMWPE). Very high molecular weight polyethylene, as used herein, refers to polyethylene having a molecular weight greater than 300,000 and less than 1,000,000. In another embodiment, polyethylene, in this invention can be cross-linked polyethylene.

Sintered polymeric plastic materials according to some embodiments of the present invention are porous. In one embodiment, for example, a sintered polymeric plastic material has a porosity ranging from about 10% to about 90%. In another embodiment, a sintered polymeric plastic material has a porosity ranging from about 20% to about 80% or from about 30% to about 70%. In a further embodiment, a sintered polymeric plastic material has a porosity ranging from about 40% to about 60%.

Porous sintered polymeric plastic media, according to some embodiments of the present invention, have an average pore size ranging from about from about 1 µm to about 200 µm. In other embodiments, porous sintered polymeric plastic materials have an average pore size ranging from about 2 µm to about 150 µm, from about 5 µm to about 100 µm, or from about 10 µm to about 50 µm. In another embodiment, a porous sintered polymeric plastic material has an average pore size less than about 1 µm. In one embodiment, a porous sintered polymeric plastic material has an average pore size ranging from about 0.1 µm to about 1 µm.

Sintered polymeric plastic materials, according to some embodiments, have a density ranging from about 0.1 g/cm$^3$ to about 1 g/cm$^3$. In other embodiments, a sintered polymeric plastic material of the present invention has a density ranging from about 0.2 g/cm$^3$ to about 0.8 g/cm$^3$ or from about 0.4 g/cm$^3$ to about 0.6 g/cm$^3$. In a further embodiment, a sintered polymeric plastic material comprising at least one plastic and at least one elastomer has a density greater than about 1 g/cm$^3$.

Elastomeric Materials that May be Used in Sintered Porous Elastomeric Media for Porous Caps and Porous Vents Elastomers suitable for use in sintered polymeric materials of the present invention, according to some embodiments, comprise thermoplastic elastomers (TPE). Thermoplastic elastomers comprise polyurethanes and thermoplastic polyurethanes (TPU). Thermoplastic polyurethanes, in some embodiments, include multiblock copolymers comprising a polyurethane and a polyester or polyether.

In other embodiments, elastomers suitable for use in sintered porous polymeric materials of the present invention comprise polyisobutylene, polybutenes, butyl rubber, or combinations thereof. In another embodiment, elastomers comprise copolymers of ethylene and other monomers such as ethylene-propylene copolymer, referred to as EPM, ethylene-octene copolymer, and ethylene-hexene copolymer. In another embodiment, elastomers comprise copolymers of propylene and other monomers such as ethylene-propylene copolymer, referred to as EPM, ethylene-octene copolymer, and polyethylene-hexene copolymer. In a further embodiment, elastomers comprise chlorinated polyethylene or chloro-sulfonated polyethylene. In a further embodiment, elastomers comprise ethylene vinyl acetate (EVA).

In some embodiments, elastomers suitable for use in sintered polymeric materials of the present invention comprise 1,3-dienes and derivatives thereof. 1,3-dienes include styrene-1,3-butadiene (SBR), styrene-1,3-butadiene terpolymer with an unsaturated carboxylic acid (carboxylated SBR), acrylonitrile-1,3-butadiene (NBR or nitrile rubber), isobutylene-isoprene, cis-1,4-polyisoprene, 1,4-poly(1,3-butadiene), polychloroprene, and block copolymers of isoprene or 1,3-butadiene with styrene such as styrene-ethylene-butadiene-styrene (SEBS). In other embodiments, elastomers comprise polyalkene oxide polymers, acrylics, or polysiloxanes (silicones) or combinations thereof.

In a further embodiment, elastomers suitable for use in sintered polymeric materials of the present invention, in some embodiments, comprise Forprene®, Laprene®, Skypel®, Skythane®, Synprene®, Rimflex®, Elexar®, Flexalloy®, Tekron®, Dexflex®, Typlax®, Uceflex®, Dexflex®, Engage®, Hercuprene®, Hi-Fax®, Innopol®, Novalene®, Kraton®, Muti-Flex®, Evoprene®, Hytrel®, Nordel®, Versify®, Vistamaxx®, Viton®, Vector®, Silastic®, Santoprene®, Elasmax®, Affinity®, Attane®, and Sarlink®.

Sintered polymeric elastomeric materials according to some embodiments of the present invention are porous. In one embodiment, for example, a sintered polymeric elastomeric material has a porosity ranging from about 10% to about 90%. In another embodiment, a sintered polymeric elastomeric material has a porosity ranging from about 20% to about 80% or from about 30% to about 70%. In a further embodiment, a sintered polymeric elastomeric material has a porosity ranging from about 40% to about 60%.

Porous sintered polymeric elastomeric materials, according to some embodiments of the present invention, have an average pore size ranging from about from about 1 µm to about 200 µm. In other embodiments, porous sintered polymeric elastomeric materials have an average pore size ranging from about 2 µm to about 150 µm, from about 5 µm to about 100 µm, or from about 10 µm to about 50 µm. In another embodiment, a porous sintered polymeric elastomeric material has an average pore size less than about 1 µm. In one embodiment, a porous sintered polymeric elastomeric material has an average pore size ranging from about 0.1 µm to about 1 µm.

Sintered polymeric elastomeric materials, according to some embodiments, have a density ranging from about 0.1 g/cm$^3$ to about 1 g/cm$^3$. In other embodiments, a sintered polymeric elastomeric material of the present invention has a density ranging from about 0.2 g/cm$^3$ to about 0.8 g/cm$^3$ or from about 0.4 g/cm$^3$ to about 0.6 g/cm$^3$. In a further embodiment, a sintered polymeric elastomeric material comprising at least one plastic and at least one elastomer has a density greater than about 1 g/cm³.

Moreover, in some embodiments, a sintered porous polymeric elastomeric material has a tensile strength ranging from about 10 to about 5,000 psi as measured according to ASTM D638. A sintered porous polymeric elastomeric material, in some embodiments, has a tensile strength ranging from about 50 to 3000 psi or from about 100 to 1,000 psi as measured according to ASTM D638. In some embodiments, a sintered porous elastomeric polymeric material has an elongation ranging from 10% to 500%.

Sintered Porous Media Comprising Both Plastic Particles and Elastomeric Particles for Porous Caps and Porous Vents A sintered polymeric material, according to some embodiments of the present invention, comprises at least one elastomer in an amount ranging from about 10 weight percent to about 90 weight percent. In other embodiments, a sintered polymeric material comprises at least one elastomer in an amount ranging from about 20 weight percent to about 80 weight percent. In another embodiment, a sintered polymeric material comprises at least one elastomer in an amount ranging from about 30 weight percent to about 70 weight percent. In a further embodiment, a sintered polymeric material comprises at least one elastomer in an amount ranging from about 40 weight percent to about 60 weight percent. In these embodiments, plastic constitutes the remainder or the majority of the remainder of the sintered polymeric material.

Sintered polymeric materials comprising at least one plastic and at least one elastomer, according to some embodiments of the present invention, are porous. In one embodiment, for example, a sintered polymeric material has a porosity ranging from about 10% to about 90%. In another embodiment, a sintered polymeric material comprising at least one plastic and at least one elastomer has a porosity ranging from about 20% to about 80% or from about 30% to about 70%. In a further embodiment, a sintered polymeric material comprising at least one plastic and at least one elastomer has a porosity ranging from about 40% to about 60%.

Porous sintered polymeric materials comprising at least one plastic and at least one elastomer, according to some embodiments of the present invention, have an average pore size ranging from about from about 1 µm to about 200 µm. In other embodiments, porous sintered polymeric materials comprising at least one plastic and at least one elastomer have an average pore size ranging from about 2 µm to about 150 µm, from about 5 µm to about 100 µm, or from about 10 µm to about 50 µm. In another embodiment, a porous sintered polymeric material has an average pore size less than about 1 µm. In one embodiment, a porous sintered polymeric material comprising at least one plastic and at least one elastomer has an average pore size ranging from about 0.1 µm to about 1 µm. Sintered polymeric materials comprising at least one plastic and at least one elastomer, according to some embodiments, have a density ranging from about 0.1 g/cm³ to about 1 g/cm³. In other embodiments, a sintered polymeric material of the present invention has a density ranging from about 0.2 g/cm³ to about 0.8 g/cm³ or from about 0.4 g/cm³ to about 0.6 g/cm³. In a further embodiment, a sintered polymeric material comprising at least one plastic and at least one elastomer has a density greater than about 1 g/cm³.

In some embodiments, a sintered polymeric material comprising at least one plastic and at least one elastomer has a tensile strength ranging from about 10 to about 5,000 psi as measured according to ASTM D638. A sintered polymeric material comprising at least one plastic and at least one elastomer, in some embodiments, has a tensile strength ranging from about 50 to 3000 psi or from about 100 to 1,000 psi as measured according to ASTM D638. In some embodiments, a sintered polymeric material comprising at least one plastic and at least one elastomer has an elongation ranging from 10% to 500%.

Antimicrobial Materials that May be Incorporated into Sintered Porous Plastic and Elastomeric Media for Porous Caps and Porous Vents.

The porous cap may have antimicrobial additives that provide antimicrobial activity and protect the liquid access ports from bacterial contamination. The antimicrobial additive can be added into the sintered porous media by sintering polymer particles with antimicrobial agents, co-sintering polymer particles with antimicrobial particles, solution coating internal and external surfaces of sintered porous polymeric media with antimicrobial agents, impregnating sintered porous polymer with antimicrobial gel, or any other appropriate method for associating the antimicrobial property with the cap.

All of the sintered porous media may contain an antimicrobial agent, or only portions of the sintered porous media may have an antimicrobial agent. Some sections of sintered porous media may be free of antimicrobial agents.

Many antimicrobial materials can be incorporated into porous media. The antimicrobial materials can be compound with polymer and then pelletized, or ground into particle shapes. Antimicrobial material could also be coated onto individual polymer particles or sintered porous media. The antimicrobial materials can be used in this invention include, but not limited to, alcohol, iodine, chlorhexidine, chlorhexidine gluconate, chlorhexidine diacetate, chlorhexidine dihydrate, biguanide polymers, phenolic based materials, such as, 5-chloro-2-(2,4-dichlorophenoxy)phenol (Triclosan), phenol, chloroxylenol (Dettol), silver based material, such as Agion, Irgaguard; zinc based materials, such as, zinc pyrithione, zinc omadine and quaternary ammonium based materials, such as benzalkonium chloride.

One specific antimicrobial material is chlorhexidine. Chlorhexidine is a biocompatible antimicrobial agent and is a 1,6-di(4-chlorophenyl-diguanido) hexane. The IUPAC name for chlorhexidine is N,N'Bis(4-chlorophenyl)-3,12-diimino-2,4,11,13-tetrazatetradecanediim-ideamide. Chlorhexidine has a high level of antibacterial activity and low mammalian toxicity. The amount of chlorhexidine in sintered porous media is from about 0.1% to about 25%, from about 0.5% to about 10%, or from about 1% to about 5% by weight.

Methods of Making a Porous Cap or a Porous Vent

When a porous cap or porous vent comprises a porous component and a non-porous component, such as an injection molded non-porous component, the porous component and the non-porous component may be attached together using techniques such as welding, through the use of adhesives or by friction coupling.

The present invention provides methods for producing a sintered polymeric media for use in a porous cap or porous vent for a medical device or a component of a medical device, for example tubing, a catheter, a luer lock, or a liquid access port. In one embodiment, providing a sintered porous polymeric media comprises providing a plurality of polymeric particles and sintering the polymeric particles.

Polymeric particles in this invention include plastic particles, elastomeric particles and combination of plastic and elastomeric particles.

Polymeric particles, in some embodiments, have average sizes ranging from about 1 µm to about 1 mm. In another embodiment, polymeric particles have average sizes ranging from about 10 µm to about 900 µm, from about 50 µm to about 500 µm, or from about 100 µm to about 400 µm. In a further embodiment, polymeric particles have average sizes ranging from about 200 µm to about 300 µm. In some embodiments, polymeric particles have average sizes less than about 1 µm or greater than about 1 mm.

Polymeric particles, in some embodiments, are sintered at a temperature ranging from about 200° F. to about 700° F. In some embodiments, polymeric particles are sintered at a temperature ranging from about 300° F. to about 500° F. The sintering temperature, according to embodiments of the present invention, is dependent upon and selected according to the identity of the polymeric particles.

Polymeric particles, in some embodiments, are sintered for a time period ranging from about 30 seconds to about 30 minutes. In other embodiments, polymeric particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of polymeric particles is administered under ambient pressure (1 atm). In other embodiments sintering of polymeric particles is administered under pressures greater than ambient pressure.

The present invention provides methods for producing a porous cap or porous vent comprising sintered polymeric materials and antimicrobial materials with antimicrobial activity for a medical device or component thereof such as an open end tubing/catheter, a luer lock, or a liquid access port. In one embodiment, a porous cap or porous vent with antimicrobial activity comprises a sintered porous polymeric component and an antimicrobial component. In one embodiment, providing a porous cap or porous vent with antimicrobial activity for a medical device or component thereof comprises providing a plurality of polymeric particles and antimicrobial particles and sintering the polymeric particles and antimicrobial particles. In another embodiment, providing a porous cap or porous vent with antimicrobial activity for a medical device or component thereof comprises providing a plurality of polymeric particles, sintering the polymeric particles and treating the sintered polymeric component with antimicrobial agents.

Antimicrobial treatments in this invention include solution coating, impregnating, and immobilizing porous media with antimicrobial agents.

Polymeric particles and antimicrobial particles, in some embodiments, have average sizes ranging from about 1 µm to about 1 mm. In another embodiment, polymeric particles and antimicrobial particles have average sizes ranging from about 10 µm to about 900 µm, from about 50 µm to about 500 µm, or from about 100 µm to about 400 µm. In a further embodiment, polymeric particles and antimicrobial particles have average sizes ranging from about 200 µm to about 300 µm. In some embodiments, polymeric particles and antimicrobial particles have average sizes less than about 1 µm or greater than about 1 mm.

Sizes of polymeric particles and antimicrobial particles, in some embodiments, are selected independently. In one embodiment, for example, the antimicrobial particles have an average size greater than the polymeric particles. In another embodiment, antimicrobial particles have an average size smaller than the polymeric particles. In a further embodiment, antimicrobial particles and antimicrobial particles have about the same average size.

Polymeric particles and antimicrobial particles, in some embodiments, are sintered at a temperature ranging from about 200° F. to about 700° F. In some embodiments, polymeric particles and antimicrobial particles are sintered at a temperature ranging from about 300° F. to about 500° F. The sintering temperature, according to embodiments of the present invention, is dependent upon and selected according to the identity of the polymeric particles and antimicrobial particles.

Polymeric particles and antimicrobial particles, in some embodiments, are sintered for a time period ranging from about 30 seconds to about 30 minutes. In other embodiments, polymeric particles and antimicrobial particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of polymeric particles and antimicrobial particles is administered under ambient pressure (1 atm). In other embodiments sintering of polymeric particles and antimicrobial particles is administered under pressures greater than ambient pressure.

In some embodiments, polymeric particles and antimicrobial particles are mixed in a desired ratio (weight percent) to produce a substantially uniform mixture. The uniform mixture of polymer and antimicrobial particles are disposed in a mold and sintered. The shape of the mold can be any desired cap or vent shapes. Polymeric particles and antimicrobial particles can be filled in the mold cavity by vibration and compression.

In some embodiments, polymeric particles and antimicrobial particles are mixed in a ratio (weight percent) of from 99.9% to 0.1%, from 99% to 1%, from 95% to 5%, from 90% to 10%, from 80% to 20%, or from 70% to 30%.

The present invention provides methods for producing a porous elastomeric cap or porous elastomeric vent with antimicrobial activity for a medical device or component thereof, such as tubing, a catheter, a luer lock or a liquid access port, the cap or vent comprising sintered elastomeric materials and antimicrobial materials. In one embodiment, a porous elastomeric cap or vent with antimicrobial activity comprises a sintered porous elastomeric component and an antimicrobial component. In one embodiment, providing a porous elastomeric cap or vent with antimicrobial activity for a medical device or component thereof comprises providing a plurality of elastomeric particles and antimicrobial particles and sintering the elastomeric particles and antimicrobial particles. In another embodiment, providing a porous elastomeric cap or vent with antimicrobial activity for a liquid access port comprises providing a plurality of elastomeric particles, sintering the elastomeric particles and treated the sintered elastomeric component with antimicrobial agents.

Elastomeric particles and antimicrobial particles, in some embodiments, have average sizes ranging from about 1 µm to about 1 mm. In another embodiment, elastomeric particles and antimicrobial particles have average sizes ranging from about 10 µm to about 900 µm, from about 50 µm to about 500 µm, or from about 100 µm to about 400 µm. In a further embodiment, elastomeric particles and antimicrobial particles have average sizes ranging from about 200 µm to about 300 µm. In some embodiments, elastomeric particles and antimicrobial particles have average sizes less than about 1 µm or greater than about 1 mm.

Sizes of elastomeric particles and antimicrobial particles, in some embodiments, are selected independently. In one embodiment, for example, the antimicrobial particles have an average size greater than the elastomeric particles. In another embodiment, antimicrobial particles have an average size smaller than the elastomeric particles. In a further embodiment, antimicrobial particles and elastomeric particles have about the same average size.

Elastomeric particles and antimicrobial particles, in some embodiments, are sintered at a temperature ranging from about 200° F. to about 700° F. In some embodiments, elastomeric particles and antimicrobial particles are sintered at a temperature ranging from about 300° F. to about 500° F. The sintering temperature, according to embodiments of the present invention, is dependent upon and selected according to the identity of the elastomeric particles and antimicrobial particles.

Elastomeric particles and antimicrobial particles, in some embodiments, are sintered for a time period ranging from about 30 seconds to about 30 minutes. In other embodiments, elastomeric particles and antimicrobial particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of elastomeric particles and antimicrobial particles administered under ambient pressure (1 atm). In other embodiments sintering of elastomeric particles and antimicrobial particles is administered under pressures greater than ambient pressure.

In one embodiment, elastomeric particles and antimicrobial particles are mixed in a desired ratio (weight percent) to produce a substantially uniform mixture. The mixture is disposed in the mold cavities. The shape of the mold cavity can be any desired cap or vent shapes. Polymeric particles and antimicrobial particles can be filled in the mold cavity by vibration and compression.

In some embodiments, elastomeric particles and antimicrobial particles are mixed in a ratio (weight percent) of from 99.9% to 0.1%, from 99% to 1%, from 95% to 5%, from 90% to 10%, from 80% to 20%, or from 70% to 30%.

The present invention provides methods for producing a porous cap or porous vent for a medical device or component thereof comprising sintered thermoplastic materials. In one embodiment, providing a sintered porous thermoplastic component comprises providing a particles of a plurality of thermoplastic particles and sintering the thermoplastic particles. Thermoplastic particles, in some embodiments, have average sizes ranging from about 1 μm to about 1 mm. In another embodiment, thermoplastic particles have average sizes ranging from about 10 μm to about 900 μm, from about 50 μm to about 500 μm, or from about 100 μm to about 400 μm. In a further embodiment, thermoplastic particles have average sizes ranging from about 200 μm to about 300 μm. In some embodiments, thermoplastic particles have average sizes less than about 1 μm or greater than about 1 mm.

Thermoplastic particles, in some embodiments, are sintered at a temperature ranging from about 200° F. to about 700° F. In some embodiments, thermoplastic particles are sintered at a temperature ranging from about 300° F. to about 500° F. The sintering temperature, according to embodiments of the present invention, is dependent upon and selected according to the identity of the thermoplastic particles.

Thermoplastic particles, in some embodiments, are sintered for a time period ranging from about 30 seconds to about 30 minutes. In other embodiments, thermoplastic particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of thermoplastic particles is administered under ambient pressure (1 atm). In other embodiments sintering of thermoplastic particles is administered under pressures greater than ambient pressure.

The present invention provides methods for producing a porous cap or porous vent with antimicrobial activity for a medical device or component thereof comprising sintered thermoplastic materials and antimicrobial materials. In one embodiment, a porous cap or porous vent with antimicrobial activity comprises a sintered porous thermoplastic component and an antimicrobial component. In one embodiment, providing a porous cap or porous vent with antimicrobial activity for a medical device or component thereof comprises providing a plurality of thermoplastic particles and antimicrobial particles and sintering the thermoplastic particles and antimicrobial particles. In another embodiment, providing a porous cap or porous vent with antimicrobial activity for a medical device or component thereof comprises providing a plurality of thermoplastic particles, sintering the thermoplastic particles, and treating the sintered thermoplastic component with antimicrobial agents. Methods of applying antimicrobial treatments in this invention include solution coating, impregnating, and immobilizing porous media with antimicrobial agents.

Thermoplastic particles and antimicrobial particles, in some embodiments, have average sizes ranging from about 1 μm to about 1 mm. In another embodiment, thermoplastic particles and antimicrobial particles have average sizes ranging from about 10 μm to about 900 μm, from about 50 μm to about 500 μm, or from about 100 μm to about 400 μm. In a further embodiment, thermoplastic particles and antimicrobial particles have average sizes ranging from about 200 μm to about 300 μm. In some embodiments, thermoplastic particles and antimicrobial particles have average sizes less than about 1 μm or greater than about 1 mm.

Sizes of thermoplastic particles and antimicrobial particles, in some embodiments, are selected independently. In one embodiment, for example, the antimicrobial particles have an average size greater than the thermoplastic particles. In another embodiment, antimicrobial particles have an average size smaller than the thermoplastic particles. In a further embodiment, antimicrobial particles and thermoplastic particles have about the same average size.

Thermoplastic particles and antimicrobial particles, in some embodiments, are sintered at a temperature ranging from about 200° F. to about 700° F. In some embodiments, thermoplastic particles and antimicrobial particles are sintered at a temperature ranging from about 300° F. to about 500° F. The sintering temperature, according to embodiments of the present invention, is dependent upon and selected according to the identity of the thermoplastic particles and antimicrobial particles.

Thermoplastic particles and antimicrobial particles, in some embodiments, are sintered for a time period ranging from about 30 seconds to about 30 minutes. In other embodiments, thermoplastic particles and antimicrobial particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of thermoplastic particles and antimicrobial particles is administered under ambient pressure (1 atm). In other embodiments sintering of thermoplastic particles and antimicrobial particles is administered under pressures greater than ambient pressure.

In some embodiments, thermoplastic particles and antimicrobial particles are mixed in a desired ratio (weight percent) to produce a substantially uniform mixture. The uniform mixture of thermoplastic particles and antimicrobial particles are disposed in a mold and sintered. The shape of the mold can be any desired shape. Thermoplastic particles and antimicrobial particles can be filled in the mold cavity by vibration and compression.

In some embodiments, thermoplastic particles and antimicrobial particles are mixed in a ratio (weight percent) of from 99.9% to 0.1%, from 99% to 1%, from 95% to 5%, from 90% to 10%, from 80% to 20%, or from 70% to 30%.

The present invention provides methods for producing a porous elastomeric cap or porous vent for a medical device or component thereof comprising sintered thermoplastic particles and elastomeric materials. In one embodiment, providing sintered porous thermoplastic particles and an elastomeric component comprises providing a plurality of thermoplastic particles and elastomeric particles and sintering the thermoplastic particles and elastomeric particles.

Thermoplastic particles and elastomeric particles, in some embodiments, have average sizes ranging from about 1 µm to about 1 mm. In another embodiment, thermoplastic particles and elastomeric particles have average sizes ranging from about 10 µm to about 900 µm, from about 50 µm to about 500 µm, or from about 100 µm to about 400 µm. In a further embodiment, thermoplastic particles and elastomeric particles have average sizes ranging from about 200 µm to about 300 µm. In some embodiments, thermoplastic particles and elastomeric particles have average sizes less than about 1 µm or greater than about 1 mm.

Thermoplastic particles and elastomeric particles, in some embodiments, are sintered at a temperature ranging from about 200° F. to about 700° F. In some embodiments, thermoplastic particles and elastomeric particles are sintered at a temperature ranging from about 300° F. to about 500° F. The sintering temperature, according to embodiments of the present invention, is dependent upon and selected according to the identity of the thermoplastic particles and elastomeric particles.

Thermoplastic particles and elastomeric particles, in some embodiments, are sintered for a time period ranging from about 30 seconds to about 30 minutes. In other embodiments, thermoplastic particles and elastomeric particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of thermoplastic particles and elastomeric particles is administered under ambient pressure (1 atm). In other embodiments sintering of thermoplastic particles and elastomeric particles is administered under pressures greater than ambient pressure.

The present invention provides methods for producing a porous elastomeric cap or vent with antimicrobial activity for a medical device or component thereof comprising sintered thermoplastic particles, elastomeric materials and antimicrobial materials. In one embodiment, a porous cap with antimicrobial activity comprises sintered porous thermoplastic particles, an elastomeric component and an antimicrobial component. In one embodiment, providing a porous cap or vent with antimicrobial activity for a medical device or component thereof comprises providing a particles of a plurality of thermoplastic particles, elastomeric particles and antimicrobial particles and sintering the thermoplastic particles, elastomeric particles and antimicrobial particles. In another embodiment, providing a porous cap or vent with antimicrobial activity for a medical device or component thereof comprises providing a plurality of thermoplastic particles and elastomeric particles, sintering the thermoplastic particles and elastomeric particles, and treating the sintered thermoplastic particles and elastomeric particles with one or more antimicrobial agents.

Antimicrobial treatments in this invention include solution coating, impregnating, and immobilizing porous media with antimicrobial agents.

Thermoplastic particles, elastomeric particles and antimicrobial particles, in some embodiments, have average sizes ranging from about 1 µm to about 1 mm. In another embodiment, thermoplastic particles, elastomeric particles and antimicrobial particles have average sizes ranging from about 10 µm to about 900 µm, from about 50 µm to about 500 µm, or from about 100 µm to about 400 µm. In a further embodiment, thermoplastic particles, elastomeric particles and antimicrobial particles have average sizes ranging from about 200 µm to about 300 µm. In some embodiments, thermoplastic particles, elastomeric particles and antimicrobial particles have average sizes less than about 1 µm or greater than about 1 mm.

Sizes of thermoplastic particles, elastomeric particles and antimicrobial particles, in some embodiments, are selected independently. In one embodiment, for example, the antimicrobial particles have an average size greater than the thermoplastic particles and the elastomeric particles. In another embodiment, antimicrobial particles have an average size smaller than the thermoplastic particles and the elastomeric particles. In a further embodiment, antimicrobial particles, thermoplastic particles and elastomeric particles have about the same average size. In one embodiment, for example, thermoplastic particles have an average size greater than elastomeric particles. In another embodiment, thermoplastic particles have an average size smaller than elastomeric particles. In a further embodiment, thermoplastic particles and elastomeric particles have about the same average size.

Thermoplastic particles, elastomeric particles and antimicrobial particles, in some embodiments, are sintered at a temperature ranging from about 200° F. to about 700° F. In some embodiments, thermoplastic particles, elastomeric particles and antimicrobial particles are sintered at a temperature ranging from about 300° F. to about 500° F. The sintering temperature, according to embodiments of the present invention, is dependent upon and selected according to the identity of the thermoplastic particles, elastomeric particles and antimicrobial particles.

Thermoplastic particles, elastomeric particles and antimicrobial particles, in some embodiments, are sintered for a time period ranging from about 30 seconds to about 30 minutes. In other embodiments, thermoplastic particles, elastomeric particles and antimicrobial particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of thermoplastic particles, elastomeric particles and antimicrobial particles is administered under ambient pressure (1 atm). In other embodiments sintering of thermoplastic particles, elastomeric particles and antimicrobial particles is administered under pressures greater than ambient pressure.

In some embodiments, thermoplastic particles, elastomeric particles and antimicrobial particles are mixed in a desired ratio (weight percent) to produce a substantially uniform mixture. The uniform mixture of polymer and antimicrobial particles are disposed in a mold and sintered. The shape of the mold can be any desired cap or vent shapes. Thermoplastic particles, elastomeric particles and antimicrobial particles can be filled in the mold cavity by vibration and compression.

In some embodiments, the ratio of the combination of total plastic or thermoplastic particles and elastomeric particles, to antimicrobial particles used in mixing these components is from 99.9% to 0.1%, from 99% to 1%, from 95% to 5%, from 90% to 10%, from 80% to 20%, or from 70% to 30% (all in weight percent (wt %)).

In some embodiments, plastic particles or thermoplastic particles and elastomeric particles are mixed in a ratio of from 95% to 5%, from 90% to 10%, from 80% to 20%, from 70% to 30%, from 60% to 40%, from 50% to 50%, from 40% to 60%, from 30% to 70%, from 20% to 80%, 10% to 90%, or 5% to 95% (all in weight percent (wt %)).

In a further aspect, the present invention provides methods of capping or venting an open end of a medical device or component thereof, such as a tube, a catheter, a luer lock, or a liquid access port with a porous polymeric cap. In one embodiment, a method for capping or venting an open end of a medical device or component thereof with a porous polymeric cap protects the medical device or component thereof from contamination. In another embodiment, a method for capping or venting an open end of a medical device or component thereof with a porous polymeric antimicrobial cap protects the medical device or component thereof from contamination. In one embodiment the medical device or component thereof is a liquid access ports including but not limited to needleless ports, catheter connectors, luer lock connectors, and urine bag outlets.

Properties of Sintered Porous Media Used in a Cap or Vent

In one embodiment, sintered porous media, including sintered porous plastic, sintered porous elastomeric or sintered porous media comprising both plastic and elastomeric material have good permeability and air flow. Good air flow, in this invention, means a sheet of sintered porous media with an average of thickness of 1 mm having Gurley number less than 1000 seconds, less than 500 seconds, less than 200 seconds, less than 100 seconds, or less than 50 seconds. The Gurley number is measured using the TAPPI T460 method as known to one of ordinary skill in the art. The Gurley number is the number of seconds for 100 cc air pass through 0.1 square inch of an open area that passes air at a pressure of 1.22 kPa.

In another embodiment, sintered porous media with 1 mm thickness, including sintered porous plastic, sintered porous elastomeric or sintered porous media comprising both plastic and elastomeric material have bacterial filtration efficiencies over 90%, over 95%, over 98%, over 99%, over 99.9% based ASTM 2101 method, as known to one of ordinary skill in the art.

In one embodiment, sintered porous media comprising antimicrobial additives, including sintered porous plastic, sintered porous elastomeric or sintered porous media comprising both plastic and elastomeric material have over three log reduction for *E coli* based on JIS 2801 test in 24 hours, as known to one of ordinary skill in the art.

In another embodiment, sintered porous media with 1 mm thickness, including sintered porous plastic, sintered porous elastomeric or sintered porous media comprising both plastic and elastomeric material do not adversely affect EO sterilization. EO sterilization can kill at least $10^6$ CFU *B. atrophaeus* in less than 120 minutes, less than 60 minutes, less than 30 minutes or less than 15 minutes EO dwell time for an area covered with the porous media.

Indicators

In one embodiment, the sintered porous cap or porous vent may have a color changing indicator. This could indicate to medical personnel that the cap or vent has been soaked with solution and may become close to leaking and may need to be changed, or that it has been exposed to a harmful bacteria or other harmful substance and may need to be changed. Potential color indicting solutions may be mixed into the material(s) forming the cap or vent. Alternatively, the cap or vent may have all or a portion of it dipped into a color changing solution.

A color change indicator comprises an inorganic or organic dye, including food grade dyes, azo compounds, or azo dyes. In some embodiments, color change indicators do not comprise inorganic salts, including transition metal salts.

In some embodiments, a color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or combinations thereof.

Color change indicators, according to some embodiments, demonstrate a pH dependency on the color produced. As a result, color change indicators, in some embodiments, indicate not only liquid contact with the barrier composition but the relative pH of the contacting liquid as well. Color change indicators demonstrating a pH dependency, in some embodiments, comprise methyl violet, eosin yellow, malachite green, thymol blue, methyl yellow, bromophenol blue, congo red, methyl orange, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or combinations thereof.

Sintered porous media of the present invention, in some embodiments, comprise at least one color change indicator in an amount ranging from about 0.001 weight percent to about 2 weight percent, from about 0.01 weight percent to about 1 weight percent, or from about 0.05 weight percent to about 0.5 weight percent of the media.

Absorbent Additives

In one embodiment, the sintered porous cap or porous vent may have a self-sealing additive.

In some embodiments, an absorbent material comprises carboxymethylcellulose (CMC), cellulose gums, hydrolyzed acrylonitrile graft copolymer, neutralized starch-acrylic acid graft copolymer, acrylamide copolymer, modified crosslinked polyvinyl alcohol, neutralized self-crosslinking polyacrylic acid, crosslinked polyacrylate salts, or neutralized crosslinked isobutylene-maleic anhydride copolymers, or salts or mixtures thereof. In other embodiments, absorbent materials comprise sodium polyacrylic acid and salts of poly(2-propenamide-co-2-propenoic acid).

In some embodiments, absorbent materials comprise those described by U.S. Pat. Nos. 5,998,032; 5,939,086; 5,836,929, 5,824,328; 5,797,347; 5,750,585; 5,175,046; 4,820,577; 4,724,114; and 4,443,515. Examples of commercially available absorbent materials include AP80HS from Stockhousen of Tuscaloosa, Ala., HYSORB® P7200 from BASF of Florham Park, N.J., and CMC under the product designation C5013 and C5678 from Sigma-Aldrich of St. Louis, Mo.

Absorbent materials, in some embodiments, can absorb greater than about 1, 50, 100, 200, 500, or 1000 percent of their weight in water while maintaining structural integrity.

Sintered porous media of the present invention, in some embodiments, comprise at least one absorbent material in an amount ranging from about 1 weight percent to about 40 weight percent of the media. In other embodiments, sintered porous media comprises an absorbent material in an amount ranging from about 5 weight percent to about 30 weight percent of the media. In a further embodiment, sintered porous media comprises an absorbent material in an amount ranging from about 10 weight percent to about 20 weight percent of the media.

Functions and Applications

Any of the various embodiments of the sintered porous caps and porous vents described above may be used in any various combinations. For example, various materials may be used to manufacture various designs and may have various additional features (e.g., antimicrobial agents or color changing indicators) incorporated therein. The caps and vents may be designed in different ways to provide different functions. Many of the functions that may be performed by various combinations of the materials and designs include but are not limited to the following.

The sintered porous media can be used as a cap or vent that prevents aerosol from passing through the cap and keeps the interior surface of the access port dry and clean.

In another embodiment, the porous cap or vent allows sterilization gas, such ethylene oxide (EO) to pass through the porous cap. This allows sterilization gas to sterilize all internal areas of the device that the porous cap covers and protects. The sterilization gas can also access the interior of medical devices with a lumen that are covered with the porous cap. This also permits EO to escape and not be trapped in certain areas. Residual EO may be deleterious to specific plastics in medical devices, for example polystyrene. Difficult to reach areas covered by the porous cap may be sterilized, for example the threads of a luer fitting. In contrast, a non-porous solid cap, such as those commercially available, would not permit sterilizing gas to reach the threads of a luer fitting.

The sintered porous media can be used as a cap or vent that can wick antiseptic media to the port or inside the port. In addition to being used for wicking the antiseptic agent, it may also be used for cleaning both the internal and external surfaces of the port by applying antiseptic liquid on the surface of the cap or vent and allowing it to wick through the cap or vent to contact internal and/or external surfaces of the port. In this way, the sintered porous plastic cap or vent functions as a delivery device for antiseptic agents.

In another embodiment, the sintered porous cap or vent may function as a bacterial barrier over vascular lines such as PICC lines, or intravenous or intraarterial lines. The porous cap blocks aerosols from accessing an area to be protected. This can also reduce the frequency of disinfecting lines by nurses or other medical personnel. Prevention of microbial access, for example bacterial access to such intravascular lines, can help prevent or decrease the frequency of infections. Preventing infections, caused by microbes such as *pseudomonas, staphylococcus* or *enterococcus* can prevent disease and suffering, save lives and save money.

In another embodiment, the sintered porous cap or vent may function as a bacterial barrier. This allows the protected section of the device from bacterial contamination for certain periods after medical packages are opened and touched.

The sintered porous media may provide better protection for bags (e.g., IV bags) that require air to enter, but must prevent bacterial entry.

In another embodiment, the sintered porous cap may function as a bacterial barrier over an end of a laparoscope.

In one embodiment, the sintered porous plastic cap is hydrophobic and can block an aqueous solution from accessing a covered area under 3 psi of pressure. Porous hydrophobic caps can also reduce the possibility of contamination caused by a liquid spill. The sintered porous hydrophobic cap may function as a leakage barrier.

In one embodiment, the sintered porous plastic cap has self-sealing capability. The porous self-sealing cap allows gas to pass through while blocking aqueous solutions from passing through. Porous self-sealing caps can reduce the possibility of contamination caused by a liquid spill. The sintered porous self-sealing cap may function as a leakage barrier.

In another embodiment, use of the porous caps of this invention simplifies the process of reducing potential contamination using a medical device. Several medical devices may be packaged and sterilized using conventional techniques. Many medical procedures have delays in opening medical packaging and using devices or some parts of the medical devices. These delays increase the chance for infection because the medical devices may be exposed to a non-sterilized environment for a period of time. Use of the porous caps of the present invention to protect medical devices within packaging reduces the contamination risk during this period of time.

For a medical device manufacturer, the procedure involves covering the luer or access ports for a medical device with a sintered porous cap of the present invention; packaging the medical device in a medical package; and sterilizing medical package in a traditional ways, especially for gas-based sterilization.

For the end user, the procedure involves opening the medical package and removing the porous cap only when the medical devices such as the covered ports or luers are needed in the medical procedure. As long as the porous caps cover the devices, ports or luers, they are kept in a sterilized condition even after the medical package containing the devices, ports or luers is opened. In this manner, nurses or other surgical assistants do not need to sterilize the medical device, such as a luer or liquid access port.

The sintered porous caps of the invention could be used on any opening of a medical device that needs sterilization and protection from contamination. Needleless liquid access ports and luers in medical devices are two non-limiting examples.

Functions of Porous Vents

In the above description, the porous vents described herein may also function as cleaning devices for medical devices or components thereof, such as a needleless access port. For example, if the porous vent is provided with one or more antimicrobial agents, it can be used for disinfection. Use of the porous vent may assist in keeping the needleless access port clean. The porous vent can be used to clean the inside surface of an access port, because the porous vent members are inserted inside the port's rubber valve. The porous vent can also wick a liquid form of antimicrobial agent into the access port.

The porous vents described in this application are good bacterial barriers, with bacterial filtration efficiencies that may be over 90%, 95%, 99%, 99.9%, 99.99% or 99.999% based on the ASTM 2101 test method. These porous vents can prevent dust and airborne bacterial deposition on medical devices or components thereof such as needleless access ports.

The porous vents described in this application can also wick antiseptic solutions. They can be disinfected by traditional 70% isopropyl alcohol (IPA) or isopropanol solution as it is needed. The porous vents can also wick the disinfection solution into the access port and disinfect the interior areas of the port. This provides better protection for the patient.

The sintered porous vent may act as a pathogen indicator.

The sintered porous vent may act as an antiseptic indicator.

The sintered porous vent may act as an aerosol barrier.

The sintered porous vent has pores and an antimicrobial agent may be entrapped inside the porous matrix for delivery to the desired surface by diffusion and migration.

The sintered porous media generally have a higher surface area than a non-porous media. This high surface area provides a higher release rate for the antimicrobial compound inside the individual polymeric particles.

The sintered porous vent has an open-cell porous structure and these open cells have tortuous paths. This structure may help maintain the gel or liquid form of antimicrobial material activity for a prolonged time.

The sintered porous vent allows air to pass, but not aerosol. As such, it keeps the target surface dry. This dry surface reduces the chance for bacterial growth. At the same time, the sintered porous vent functions as an aerosol barrier to prevent airborne bacterial deposition on the target surface.

The elastomeric properties of some porous vents allow the porous vents to be squeezed in order to release the antimicrobial media onto the targeted surface.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Air Flow (Gurley) and Bacterial Filtration Efficiency (BFE) for Different Sintered Porous Media for Use in Caps and Vents Table 1 presents data for air flow (Gurley) and bacterial filtration efficiency (BFE) for different sintered porous media. These materials are examples for a porous cap. Other materials or combinations of other materials can be made into porous caps for the purposes of this invention. Gurley numbers were measured by 4340 automatic densometer.

The test data were the number of seconds for 100 ml of air passing through a 0.1 square inch orifice at 4.88 inch water pressure. TPTT means too porous to test, indicating the porous media is very open to the air. BFE data were collected following ASTM F2101 method. The data indicate that sintered porous media can significantly reduce the bacterial penetration through the media and allow the gas the pass through. Sintered porous media have much higher air flow than traditional medical packaging materials, such as Tyvek® or paper. Sintered porous media provide an excellent combination of properties that prevent potential contamination and permit chemical sterilization. Sintered porous media fit in current medical device packages. Sintered porous media provide secondary protection for the key areas from contamination after main packages are open.

The sintered porous plastic media are 100% porous polyethylene, including UHMWPE and HDPE. The self-sealing parts were made from 90% UHMWPE and 10% carboxymethylcellulose (CMC).

TABLE 1

Gurley numbers and BFEs for different sintered porous media.
Gurley and BFE

| Description | Pore size (microns) | Thickness | Gurley number | BFE % |
|---|---|---|---|---|
| Sintered self-sealing part | 18 | 2.5 mm | 120 | >99.9 |
| Sintered porous plastic | 8 | 1.65 mm | 143 | >99.9 |
| Sintered porous plastic | 14 | 1.7 mm | 95 | >99.9 |
| Sintered porous plastic | 30 | 3.4 mm | 22 | 98 |
| Sintered porous plastic | 70 | 3.4 mm | TPTT | 86 |
| Sintered porous plastic | 110 | 3.4 mm | TPTT | 70 |

Example 2

Antimicrobial Properties for Sintered Porous Media with Chlorhexidine (CHX) Additive Tables 2-4 list antimicrobial properties for sintered porous media with chlorhexidine (CHX) additive. The data indicate sintered porous media are effective to kill HAI related microbes. These sintered media are made of UHMWPE and alloys of polyethylene and chlorhexidine.

TABLE 2

Sintered porous media anti-*Staphylococcus aureus* properties based on the JIS 2801 test.

| Product | Initial CFU | 24 hrs CFU | % Reduction | Log Reduction |
|---|---|---|---|---|
| Negative control | $3.3 \times 10^6$ | $3.7 \times 10^6$ | −13 | −0.05 |
| Sintered Porous media without CHX | $3.3 \times 10^6$ | $3.4 \times 10^6$ | −2 | −0.01 |
| Sintered porous media with 1% CHX | $3.3 \times 10^6$ | <200 | >99.994 | >4.22 |
| Sintered porous media with 2% CHX | $3.3 \times 10^6$ | <200 | >99.994 | >4.22 |

These sintered media are made of UHMWPE and alloys of polyethylene and chlorhexidine.

TABLE 3

Sintered porous media anti-*E coli* properties based on the JIS 2801 test.

| Product | Initial CFU | 24 hrs CFU | % Reduction | Log Reduction |
|---|---|---|---|---|
| Negative control | $2.4 \times 10^6$ | $2.9 \times 10^7$ | −1212 | −1.12 |
| Sintered porous media without CHX | $2.4 \times 10^6$ | $2.8 \times 10^7$ | −1075 | −1.07 |
| Sintered porous media with 1% CHX | $2.4 \times 10^6$ | <200 | >99.9915 | >4.07 |
| Sintered porous media with 2% CHX | $2.4 \times 10^6$ | <200 | >99.9915 | >4.07 |

These sintered media are made of UHMWPE and alloys of polyethylene and chlorhexidine.

TABLE 4

Sintered porous media anti-*Candida albicans* properties based on JIS 2801 test.

| Product | Initial CFU | 24 hrs CFU | % Reduction | Log Reduction |
|---|---|---|---|---|
| Negative control | $1.8 \times 10^6$ | $5.8 \times 10^5$ | 67 | 0.48 |
| Sintered porous media with 1% CHX | $1.8 \times 10^6$ | 5 | 99.99973 | 5.56 |
| Sintered porous media with 2% CHX | $1.8 \times 10^6$ | 0 | >99.999945 | >6.26 |

Example 3

Ethylene Oxide Comparative Resistance Test

Four types of sintered porous plastic caps were made under normal sintering conditions. The caps were designed to fit 7 ml scintillation glass vials (VWR, Radnor, Pa.). The interior of each glass vial was inoculated at one site with a population of at least of $1.0 \times 10^6$ colony forming units (CFU)/site of *Bacillus atrophaeous* with Steris® Spordex spore strip. (BI means biological indicator) After inoculation, each glass vials was assembled with a porous cap or without a cap and packaged in a 4"×9" Tyvek® pouch. All samples were sterilized in a STERIS® model 3017 unit 100% EO sterilizer with following conditions:
Conditioning Phase Set point:
Temperature: 54.0° C.
Initial Vacuum: 1.3 pounds per square inch absolute (psia)
Relative Humidity (RH): 50%
Humidity Set Point: 2.4 psia
Steam Swell Time: 60 minutes
Exposure Phase Set Points:
Temperature: 54.0° C.
Sterilant Set point: 7.8 psia
EO Concentration: 600 mg/L
Gas Dwell Time: 5, 15, 30, 60, 90 and 180 minutes
Immediately following the completion of each cycle, the BI contained in each glass vial was tested for sterility by aseptically immersing it into 20 ml containers of soybean casein digest broth (SCDB). The containers were then incubated at 30-35° C. for a minimum of seven days and scored for growth of indicator organism, *B. atrophaeus*. Five replicates were run for each porous cap at each duration of gas dwell time.

All vials with porous caps showed sterility after 30 minutes of EO exposure time. Since current medical device EO sterilization process requires hours EO exposure time for sterility, this indicates porous caps do not negatively affect current medical device's EO sterilization process.

The vials without a cap, with a porous polyethylene (PE) cap of average pore size of 25 microns and 35% pore volume, and with a PE self-sealing cap of average pore size of 22 microns and pore volume of 35% showed sterility at 15 minutes EO cycle. This indicates that porous caps do not negatively the affect EO sterilization process since these vials with porous caps were very similar to the vials without any cap. Porous PE caps with 12 microns pore size and 31% pore volume also showed sterility at 30 minutes EO sterilization time. Table 5 lists the test results for the vials without caps and vials with different porous caps at different EO exposure times. Combined with over 99% aerosol bacterial barrier properties of these sintered porous materials, these sintered porous caps significantly reduce the chance of infection at liquid access ports of medical device.

TABLE 5

Comparative ethylene oxide test results with and without porous media in caps.

| Vials | Pore size/Pore volume (μm)/% | 5 minutes | 15 minutes | 30 minutes | 60 minutes | 90 minutes | 180 minutes |
|---|---|---|---|---|---|---|---|
| No cap | NA | +, +, +, +, + | 0, 0, 0, 0, 0 | 0, 0, 0, 0, 0 | 0, 0, 0, 0, 0 | 0, 0, 0, 0, 0 | 0, 0, 0, 0, 0 |
| Porous EVA cap | 155/29 | +, +, +, +, + | +, +, 0, 0, 0 | 0, 0, 0, 0, 0 | 0, 0, 0, 0, 0 | 0, 0, 0, 0, 0 | 0, 0, 0, 0, 0 |
| Porous PE cap | 25/35 | +, +, +, +, + | 0, 0, 0, 0, 0 | 0, 0, 0, 0, 0 | 0, 0, 0, 0, 0 | 0, 0, 0, 0, 0 | 0, 0, 0, 0, 0 |
| Porous PE Self-sealing cap | 22/35 | +, +, +, +, + | 0, 0, 0, 0, 0 | 0, 0, 0, 0, 0 | 0, 0, 0, 0, 0 | 0, 0, 0, 0, 0 | 0, 0, 0, 0, 0 |
| Porous PE Cap | 12/32 | +, +, +, +, + | +, 0, 0, 0, 0 | 0, 0, 0, 0, 0 | 0, 0, 0, 0, 0 | 0, 0, 0, 0, 0 | 0, 0, 0, 0, 0 |

In this table, + indicates bacterial growth was observed, 0 indicates no bacterial growth was observed.

All patents, publications and abstracts cited above are incorporated herein by reference in their entirety. It should be understood that the foregoing and the figures relate only to preferred embodiments of the present invention and that numerous modifications or alterations may be made therein without departing from the spirit and the scope of the present invention as defined in the following claims.

The invention claimed is:

1. A device for covering an opening of a medical device, the device comprising a sintered porous cap body comprising a device cooperating end integral with a porous closed end, the entirety of the sintered porous cap body comprising a combination of plastic particles and elastomeric particles producing a substantially uniform mixture that is sintered in a mold in the shape of the cap body, the porous cap having a porosity of between 10% to about 90% after sintering such that sterilizing gas can pass through the porous cap, the porous closed end providing a physical cover over the opening of the medical device in use, the porous cap comprising a bacterial filtration efficiency of over 95% based on the ASTM 2101 test method and an air flow having a Gurley number less than 200 seconds measured using the TAPPI T460 method.

2. The device of claim 1, further comprising an antimicrobial additive, a color change indicator, an antiseptic, an absorbent material or a combination thereof.

3. The device of claim 1, wherein the sintered porous cap is configured to be screwed onto an access port, capped onto an access port by stretching, or plugged into an access port by a frictional fit.

4. The device of claim 1, wherein the sintered porous cap permits sterilizing gas to pass through the porous cap and contact the portion of the medical device.

5. The device of claim 1, wherein the medical device is a liquid access port.

6. The device of claim 5, wherein the liquid access port has a luer fitting or a connector.

7. The device of claim 5, wherein the liquid access port is connected to an intravascular line, a cerebrovascular line, a gastrointestinal line, a peripherally inserted central catheter, a urinary catheter, a drainage tube, a shunt, a PEG tube, a PEG-J tube, a nasogastric tube, or an endotracheal tube or another tube.

8. The device of claim 1, wherein the sintered porous cap prevents microbes from entering the medical device, thereby retarding or preventing microbial contamination of the medical device.

9. The device of claim 1, wherein the sintered porous cap comprises an average pore size ranging from about 1 μm to about 200 μm.

10. The device of claim 1, wherein the sintered porous cap comprises a density ranging from about 0.1 g/cm$^3$ to about 1 g/cm$^3$.

11. The device of claim 1, wherein the sintered porous cap comprises a polyolefin.

12. The device of claim 11, wherein the polyolefin comprises polyethylene, ultrahigh molecular weight polyethylene, or high density polyethylene.

13. The device of claim 1, wherein the medical device is a liquid access port, connector, line, catheter or tube selected from the group consisting of an intravascular line, a cerebroventricular line, a gastrointestinal line, a peripherally inserted central catheter, a urinary catheter, a drainage tube, a shunt, a PEG tube, a PEG-J tube, a nasogastric tube, and an endotracheal tube.

14. The device of claim 1, wherein the device cooperating end comprises an attachment feature for attachment of the sintered porous cap body to the opening of the medical device.

15. The device of claim 14, wherein the attachment feature comprises threads, a stretchable cap portion, a friction fit portion, or a snap fit and lock mechanism.

16. A device for covering an opening of a medical device, the device comprising a sintered porous cap body comprising a device cooperating end integral with a porous closed end, the entirety of the sintered porous cap body comprising a combination of plastic particles and elastomeric particles wherein the sintered porous cap comprises an average pore size ranging from about 1 μm to about 200 μm, the porous closed end providing a physical cover over the opening of the medical device in use, the porous cap comprising a bacterial filtration efficiency of over 95% based on the ASTM 2101 test method and an air flow having a Gurley number less than 200 seconds measured using the TAPPI T460 method.

17. A device for covering an opening and side portions of a medical device, the device comprising a sintered porous cap body comprising a device cooperating end integral with a porous closed end, the entirety of the sintered porous cap body comprising a combination of plastic particles and elastomeric particles, wherein the sintered porous cap comprises a porosity that permits sterilizing gas to pass through the porous cap and contact the opening and side portions of the medical device, the porous cap comprising a bacterial filtration efficiency of over 95% based on the ASTM 2101 test method and an air flow having a Gurley number less than 200 seconds measured using the TAPPI T460 method.

* * * * *